US006524627B1

(12) United States Patent
Kim et al.

(10) Patent No.: US 6,524,627 B1
(45) Date of Patent: Feb. 25, 2003

(54) PHARMACEUTICAL COMPOSITION FOR PREVENTING AND TREATING ALLERGIC DISEASES AND A METHOD FOR PREPARATION THEREOF

(75) Inventors: Hyung-Min Kim, Cheollabook-do (KR); Chul-Ho Jang, Jeollabook-do (KR); Woo-Jun Hwang, Cheollabook-do (KR); Eun-Jeung Park, Cheollabook-do (KR)

(73) Assignees: Daehan Biolink Co., Ltd., Chungbuk (KR); Biomedpark Co., Ltd., Yongin (KR)

( * ) Notice: Subject to any disclaimer, the term of this patent is extended or adjusted under 35 U.S.C. 154(b) by 0 days.

(21) Appl. No.: 10/101,468

(22) Filed: Mar. 20, 2002

(51) Int. Cl.[7] .......................... A01N 65/00; A61K 35/78
(52) U.S. Cl. ...................... 424/741; 424/725; 424/747; 424/769; 424/773; 424/775; 424/776; 424/777
(58) Field of Search ................ 424/741, 725, 424/777, 773, 769, 775, 747, 776

(56) References Cited

U.S. PATENT DOCUMENTS

| | | | | |
|---|---|---|---|---|
| 6,027,728 A | * | 2/2000 | Yuen | 424/74 |
| 6,045,800 A | * | 4/2000 | Kim et al. | 514/900 |
| 6,162,459 A | * | 12/2000 | Hu | 424/449 |

OTHER PUBLICATIONS

Hyun–Ja Jeong et al., "Effects of Allergina on the Treatment of Otitis Media with Effusions", Inflammation, Vo. 26, No. 2, Apr. 2002.
Hyun–Ja Jeong et al., "Effect of allergina on Mast Cell–Mediated Allergic Reactions", Immunopharmacology and Immunotoxicology. 23(4), 627–637 (2001).

* cited by examiner

*Primary Examiner*—Herbert J. Lilling
(74) *Attorney, Agent, or Firm*—Birch Stewart Kolasch & Birch LLP

(57) ABSTRACT

This invention relates to a pharmaceutical composition comprising Platycodi Radix, Scutellariae Radix, Ponciri Fructus, Schizonepetae Herba, Bupleuri Radix, Angelicae dahuricae Radix, Paeoniae Radix alba, Cnidii Rhizoma, Angelicae gigantis Radix, Ledebouriellae Radix, Forsythiae Fructus, Glycyrrhizae Radix, Lonicerae Flos, Taraxaci Herba, Trichosanthis Radix, Ulmi Cortex Radicis, Astragali Radix, Atractylodis Rhizoma alba, Rehmanniae Rhizoma, Zanthoxyli Fructus, Magnoliae Flos, Xanthii Fructus, Mori Cortex Radicis, Pinelliae Tuber, Cimicifugae Rhizoma, Puerariae Radix and Menthae Herba as the active ingredients for preventing and/or treating acute and/or chronic allergic nasal diseases (including chronic paranasal sinusitis), allergic dermatitis, allergic otitis media (including recurrent otitis media with effusions), allergic conjunctivitis, allergic asthma, etc., and to a method for preparation thereof.

7 Claims, No Drawings

PHARMACEUTICAL COMPOSITION FOR PREVENTING AND TREATING ALLERGIC DISEASES AND A METHOD FOR PREPARATION THEREOF

BACKGROUND OF THE INVENTION

1. Field of the Invention

This invention relates to a pharmaceutical composition for preventing and treating allergic diseases and to a method for preparation thereof. Specifically, the present invention relates to a pharmaceutical composition comprising Platycodi Radix, Scutellariae Radix, Ponciri Fructus, Schizonepetae Herba, Bupleuri Radix, Angelicae dahuricae Radix, Paeoniae Radix alba, Cnidii Rhizoma, Angelicae gigantis Radix, Ledebouriellae Radix, Forsythiae Fructus, Glycyrrhizae Radix, Lonicerae Flos, Taraxaci Herba, Trichosanthis Radix, Ulmi Cortex Radicis, Astragali Radix, Atractylodis Rhizoma alba, Rehmanniae Rhizoma, Zanthoxyli Fructus, Magnoliae Flos, Xanthii Fructus, Mori Cortex Radicis, Pinelliae Tuber, Cimicifugae Rhizoma, Puerariae Radix and Menthae Herba as the active ingredients for preventing and/or treating acute and/or chronic allergic nasal diseases (including chronic paranasal sinusitis), allergic dermatitis, allergic otitis media (including recurrent otitis media with effusions), allergic conjunctivitis, allergic asthma, etc., and to a method for preparation thereof.

2. Description of the Prior Art

A normal immune reaction may cause local inflammations or eliminate foreign substance without damaging tissues of their hosts by stimulating effective molecules to remove attacks from allergen through various mechanisms. However, the term of hypersensitivity or allergy is used when an immune reaction is excessively activated or progressed in an undesirable direction to harm the human body. Today, allergic diseases cost a lot of money, because they tend to be more severe in civilized societies. According to a literature [Scientific American, September, 1993], more than 20% of American people are suffering from various allergic symptoms, and allergic rhinitis is the most common form of allergy. The attack of allergen can sometimes be fatal. According to the statistical data of 1990, it was reported that 3.6 billion dollars had been spent to the direct medical cost for asthma. As to the number of patients who are suffering from these allergic diseases, Korea is also on the similar level to the developed countries. The number is increasing every year. In particular, young child patients are on rapid increase. Thus, many researchers are devoting themselves in developing a drastic cure to reduce economic, biological and physical burden of the patient from such allergic diseases.

It might be said that diversity and complexity of allergic diseases are from the exposure to many kinds of allergen in the modern life. Synthetic fibers such as nylon and Teflon, and synthetic resins such as polyethylene, polyester and epoxy resin, which brought innovation to the textile industry, cause anaphylactic contact dermatitis at skin or mucous membrane by various chemical substances like monomer and polymer that are produced in the manufacturing process. On the other hand, allergic inflammations on the skin are caused by contact with glass frames, artificial teeth, wrist watch chains, plastic raincoats, umbrella handles, etc. The substances such as polyurethane, which are widely used as paints for cars, furniture and musical instruments, are the main cause of bronchial asthma. Rubber, leather, cement, and metals such as platinum, gold, mercury and nickel may cause allergic contact dermatitis. Accessories, such as earrings, necklace and finger rings, or rubber products, may also cause allergy. It is well known that fast food, antiseptic, synthetic sweetening, and additives including food colors may also cause food allergy.

Moving into the age of synthetic medicine from that of natural medicine in which raw materials were the roots of herbs and the barks of trees, antibiotic shocks and drug allergies by chemical substances (e.g. sulfas, salicylic acids, pyrazolon and local anesthetic) and enzymatic substances have been frequently occurred. It has been revealed that the pathogenesis of food and drug allergy could occur in all types of hypersensitivity immune reactions I, II, III, and IV. Allergy to cosmetic materials has become common. Bronchial asthma has been rapidly increased since the environmental pollution has caused or worsened respiratory allergic diseases. Today, occupational allergies also draw our attention. We can take numerous examples of such occupational allergies as bakery asthma, dandruff asthma, librarian asthma of librarians, wood asthma of carpenters, poultry farming asthma, and contact dermatitis of welders.

The initial stage of allergic reaction is development of IgE antibody that makes a strong combination with the mast cell or receptors on the surface of basophilic leukocyte. After the antigen (allergen) eaten by antigen-presenting cells such as macrophages was processed, the peptide presented by MHC class II molecule on the surface of membrane is recognized by receptors on the surface of T-cell(TCR). Cell-activating substance (cytokines), such as IL-2, IFN-v and TNF (tumor necrosis factor)-$\beta$(derived from Th1-cells), and IL-4, IL-5, IL-6, IL-9 and IL-10 (derived from Th2-cells), are produced in the activated T-cells. The produced cell-activating substance acts on T and B cells to participate in proliferation and differentiation. Then, B-cells are activated by the combination of CD40 ligand (CD40L) on T-cells and CD 40 on B-cells. Furthermore, as IL-4 derived from T-cells is added, B-cells are differentiated into IgE-producing cells by a class switch. In the mast cells, two molecules of IgE are combined with polyvalent antigen to form a bridge on the receptors of membrane, leading to a series of biochemical processes causing degranulation. Various chemical media such as histamine are secreted from the mast cell by degranulation, and may increase the permeability of capillary, contract the smooth muscle, and enhance the mucus secretions, together with prostaglandins and leukotrienes produced newly by arachidonic acid metabolism within the membrane, which results in the followings: pruritus, flare, urticaria and angioedema on the skin; coughing, suffocating, chest tightness, respiratory difficulties. and cyanosis in the respiratory tract; paling, hypotension and arrhythmia in, cardiovascular system; nausea, vomiting and diarrhea in GI tract; and paresthesia, vertigo, headache, convulsion and loss of consciousness in the nerve system.

Chronic paranasal sinusitis as an example of allergic disease, which frequently occurs in an allergic constitution, may cause a nasal polyp when nasal hypertrophy gets more severe by irreversible changes such as desquamation, regression and coagulation of the blood vessel to the epidermis of mucous membrane on occurring the repetitive acute paranasal sinusitis. The chronic paranasal sinusitis poorly responds to internal medicines including antibiotic, and surgical operations for young children are not recommended because the paranasal sinuses of young children are in the development. Although adult patients can get surgical operations for the chronic paranasal sinusitis, the disease may easily recur if a drastic treatment for cold is not accompanied by immune reinforcement.

Also, otitis media is another common disease that occurs more than once in 70% of the infants, and about 10% of acute otitis media are progressed to the chronic stage in spite of antibiotic treatment. The recurrent otitis media with effusions (ROMEs) occurs when young children with weak immunity are exposed to upper respiratory infection before chronic otitis media are completely cured. The ROMEs tend to be increased if prolonged and may cause severe posteffects such as hearing disturbance, adhesion of tympanic membrane, and destruction of bone structure. In the young children with allergic constitution and weak immunity, the repeated colds by virus and secondary bacterial infection serve as complicated factors for ROME together with chronic paranasal sinusitis, adenoid hypertrophy, and middle ear ventilation problem by eustachian obstruction.

The medicines used currently in alleviating various allergic symptoms have the problem that the effects thereof are temporary, and some side effects may occur by a long-term therapy. The antibiotics cannot affect the inhibition of IL-6 that is known for playing an important role in pathogenesis of chronic mucous exudates that are progressed in young children. A report shows that IL-6 could be controlled through antibiotic and steroids for a long period of time. However, administration of antibiotics and steroids for a long time may cause such side effects as suppressing immune function of the whole body.

The present inventors have made extensive clinical researches and experiments in view of a medical treatment method of Bujungkusa (curing pathogenic factors by encouraging normal immune power of the human body) with the intention to prevent and cure various allergic diseases in a radical way without any side effect. As a result, the inventors have found that a suitable combination of specific herbs has an excellent antiallergic effect without common side effects above mentioned, and completed the present invention. In particular, the composition according to the present invention may increase immunity to cure paranasal sinusitis, control allergy, and minimize the possibility for young children to catch colds.

SUMMARY OF THE INVENTION

The present invention provides a pharmaceutical composition for preventing and treating allergic diseases comprising an extract of mixture including Platycodi Radix, Scutellariae Radix, Ponciri Fructus, Schizonepetae Herba, Bupleuri Radix, Angelicae dahuricae Radix, Paeoniae Radix alba, Cnidii Rhizoma, Angelicae gigantis Radix, Ledebouriellae Radix, Forsythiae Fructus, Glycyrrhizae Radix, Lonicerae Flos, Taraxaci Herba, Trichosanthis Radix, Ulmi Cortex Radicis, Astragali Radix, Atractylodis Rhizoma alba, Rehmanniae Rhizoma, Zanthoxyli Fructus, Magnoliae Flos, Xanthii Fructus, Mori Cortex Radicis, Pinelliae Tuber, Cimicifugae Rhizoma, Puerariae Radix and Menthae Herba. Preferably, the present composition further comprises more than one selected from a group consisting of Atractylodis Rhizoma, Aurantii Nobilis Pericarpium, Amomi Semen, Myristicae Semen, Mume Fructus, Asiasari Radix, Akebiae Caulis, Raphani Semen and Cocicis Semen.

DETAILED DESCRIPTION

The active ingredients of the present composition have the following effects and/or fuction: Platycodi Radix has expectorant and/or drain, and defervescence effects; Scutellariae Radix has anti-inflammatory, defervescence, analgesic, antiseptic, antihypersensitivity, and antiviral effects; Ponciri Fructus has effects of relieving stagnation and antiallergic effect; Schizonepetae Herba has anti-inflammatory effects for, pharyngitis, and itching relieving, and antimicrobial effects; Bupleuri Radix has sweat-promoting and digesting, spasmolytic, analgesic, defervescence, mucolytic, and anti-inflammatory effects; Angelicae dahuricae Radix has nasal obstruction relieving, detumescence and analgesic effects; Paeoniae Radix alba has sedative, spasmolytic, defervescence, analgesic, antimicrobial, anti-inflammatory and vasodilatory effects; Cnidii Rhizoma has effects of promoting healing and blood flow; Angelicae gigantis Radix has blood-nourishing and moistening, sedative, analgesic and antimicrobial effects; Ledebouriellae Radix has calming, analgesic, antimicrobial and anti-inflammatory effects; Forsythiae Fructus has calming, anti-inflammatory, drain, analgesic, vitalizing and detumescence effects; Glycyrrhizae Radix has mucolytic, expectorant, detoxification, spasmolytic, anti-inflammatory, analgesic and antihypersensitivity effects; Lonicerae Flos has calming, detoxification, vitalizing and blood flow promoting effects; Taraxaci Herba has calming, detoxification, anti-inflammatory, antimicrobial, antiviral, antifungal, and diuresis effects; Trichosanthis Radix has fluid producing, moistening, detumescence, and drain effects; Ulmi Cortex Radicis has detumescence, detoxification, antipyretic, and anti-inflammatory effects; Astragali Radix. has Ki-replenishing, toxin weakening, drain and, analgesic effects; Atractylodis Rhizoma alba has spleen-tonificating and replenishing, drying and diuresis, and sweat-suppressing effects; Rehmanniae Rhizoma has calming, blood-tonificating and fluid producing effects; Zanthoxyli Fructus has effects for warming the spleen and stomach to dispel cold and relieving nasal obstruction; Magnoliae Flos and Xanthii Fructus have effects for removing cold sense and relieving nasal obstruction; Mori Cortex Radicis has effects for purging heat the lung and anti-asthma, diuresis and detumescence; Pinelliae Tuber has effects for moistening and expectorant; Cimicifugae Rhizoma has effects for calming and detoxification; Puerariae Radix has an effect of vitalizing, and Menthae Herba has wind-dispelling, antipyretic, and throat-refreshing effects.

The additional ingredients of the present composition have the following effects: Atractylodis Rhizoma has effects for invigorating spleen and drying; Aurantii Nobilis Pericarpium has vitalizing & drying, expectorant, antitussives, and mucolytic effects; Amomi Semen has drying and healing-promoting, spleen-warming and diarrhea-relieving effects; Myristicae Semen has spleen-warming, healing-promoting, astringent and diarrhea-relieving effects; Mume Fructus has anti-inflammatory, astringent and fluid-producing effects; Asiasari Radix has effects for warming lung & resolving phlegm, diverging wind-cold and analgesic; Akebiae Caulis has effects for promoting normal flow and emaciation; Raphani Semen has effects for promoting digestion, checking upward perverted Ki, and expectorant; Cocicis Semen has calming, drain, emaciation, detumescence, invigorating spleen, and anti-inflammatory effects.

The present composition contains Platycodi Radix, Scutellariae Radix, Ponciri Fructus, Schizonepetae Herba, Bupleuri Radix, Angelicae dahuricae Radix, Paeoniae Radix alba, Cnidii Rhizoma, Angelicae gigantis Radix, Ledebouriellae Radix, Forsythiae Fructus, Glycyrrhizae Radix, Lonicerae Flos, Taraxaci Herba, Trichosanthis Radix, Ulmi Cortex Radicis, Astragali Radix, Atractylodis Rhizoma alba, Rehmanniae Rhizoma, Zanthoxyli Fructus, Magnoliae Flos, Xanthii Fructus, Mori Cortex Radicis, Pinelliae Tuber, Cimicifugae Rhizoma, Puerariae Radix and Menthae Herba, preferably in a ratio of 4–6:2–4:3:3:3:3:4–6:4:4–8:2:2–6:4–8:6–12:8–12:4:6–12:6–10:4–8:4–8:2:2–

4:4–6:4–6:4:2–4:4–8:2. The present composition further contains more than one selected from the group consisting of Atractylodis Rhizoma, Aurantii Nobilis Pericarpium, Amomi Semen, Myristicae Semen, Mume Fructus, Asiasari Radix, Akebiae Caulis, Raphani Semen and Cocicis Semen preferably in a ratio of 4:4:4:4:2–4:2:3:4:8–10.

The present inventors through many clinical and animal experiments have determined the ratio of the ingredient herbs. In the event that the proportion of each herb is below the lower limit of proportion, its pharmaceutical effect is drastically decreased. On the other hand, if it is above the higher limit of proportion, synergistic and cooperative effects among ingredient herbs are decreased due to decrease of pharmacological effects of other ingredients.

The pharmaceutical composition of this invention may be used for preventing and treating allergic diseases such as acute or chronic allergic rhinitis (including chronic paranasal sinusitis), allergic dermatitis, allergic otitis media (including ROME), allergic conjunctivitis, and allergic asthma. These pharmacological effects of the present composition are proved by Experiments 1–4 below. The pharmacological mechanism of the present composition has not been exactly revealed yet, but can be inferred that the present composition suppresses local and systemic allergic reactions of the human body by controlling generation of cell-activating substances and chemical media produced in the immune cells.

The pharmaceutical composition of the present invention may be prepared by mixing pharmaceutically acceptable carriers with the extract of mixture including Platycodi Radix, Scutellariae Radix, Ponciri Fructus, Schizonepetae Herba, Bupleuri Radix, Angelicae dahuricae Radix, Paeoniae Radix alba, Cnidii Rhizoma, Angelicae gigantis Radix, Ledebouriellae Radix, Forsythiae Fructus, Glycyrrhizae Radix, Lonicerae Flos, Taraxaci Herba, Trichosanthis Radix, Ulmi Cortex Radicis, Astragali Radix, Atractylodis Rhizoma alba, Rehmnanniae Rhizoma, Zanthoxyli Fructus, Magnoliae Flos, Xanthii Fructus, Mori Cortex Radicis, Pinelliae Tuber, Cimicifugae Rhizoma, Puerariae Radix and Menthae Herba. The extract may be obtained by decocting herbal medicines with conventional suitable solvents according to physical and chemical properties, and may be concentrated and dried to powder.

The present composition may be formulated into the forms of pills, granules, spray, liquid, etc., using conventional preparation methods. The present composition is preferably in a form of liquid in view of effectiveness, but it may be prepared in the form of pills, granules, spray, suppository, tablet, or capsules, and may be changed to any other form, if desired.

The present composition may be prepared by the following method: for example, adding 1000 ml of water to the mixture including 4–6 g of Platycodi Radix, 2–4 g of Scutellariae Radix, 3 g of Ponciri Fructus, 3 g of Schizonepetae Herba, 3 g of Bupleuri Radix, 3 g of Angelicae dahuricae Radix, 4–6 g of Paeoniae Radix alba, 4 g of Cnidii Rhizoma, 4–8 g of Angelicae gigantis Radix, 2 g of Ledebouriellae Radix, 2–6 g of Forsythiae Fructus, 4–8 g of Glycyrrhizae Radix, 6–12 g of Lonicerae Flos, 8–12 g of Taraxaci Herba, 4 g of Trichosanthis Radix, 6–12 g of Ulmi Cortex Radicis, 6–10 g of Astragali Radix, 4–8 g of Atractylodis Rhizoma alba, 4–8 g of Rehmanniae Rhizoma, 2 g of Zanthoxyli Fructus, 2–4 g of Magnoliae Flos, 4–6 g of Xanthii Fructus, 4–6 g of Mori Cortex Radicis, 4 g of Pinelliae Tuber, 2–4 g of Cimicifugae Rhizoma, 4–8 g of Puerariae Radix and 2 g of Menthae Herba, optionally with 4 g of Atractylodis Rhizoma, 4 g of Aurantii Nobilis Pericarpium, 4 g of Amomi Semen, 4 g of Myristicae.Semen, 2-4 g of Mume Fructus, 2 g of Asiasari Radix, 3 g of Akebiae Caulis, 4 g of Raphani Semen and 8–10 g of Cocicis Semen, and decocting the mixture for 1.5 hour to be concentrated to 150 ml of decoction. The suitable dose is 1.5–2 ml per kg of body weight and is administrated 3 times a day. For example, a young child weighted 20 kg takes 30–40 ml of the decoction 3 times a day. However, the dose of the present composition is varied depending on weight, age, sex, seriousness of disease, and a patient's ability to digest. Further, the other formulation of the present composition may be administrated orally or parenterally by an appropriate dose.

In taking the present composition, patients with chronic allergic disease should take it consecutively for an average of 3 months, ones with a chronic paranasal sinusitis for an average of 4 months, ones with allergic ROME for an average of 3 months, and ones with atopic dermatitis for an average of 5 months.

The present invention will be explained in detail by the following Examples, which are not intended to limit the present invention.

EXAMPLE 1

Preparation of Decoction 1000 ml of water was added to the mixture including 5 g of Platycodi Radix, 3 g of Scutellariae Radix, 3 g of Ponciri Fructus, 3 g of Schizonepetae Herba, 3 g of Bupleuri Radix, 3 g of Angelicae dahuricae Radix, 5 g of Paeoniae Radix alba, 4 g of Candii Rhizoma, 6 g of Angelicae gigantis Radix, 2 g of Ledebouriellae Radix, 4 g of Forsythiae Fructus, 6 g of Glycyrrhizae Radix, 9 g of Lonicerae Flos, 10 g of Taraxaci Herba, 4 g of Trichbsanthis Radix, 9 of Ulmi Cortex Radicis, 8 g of Astrgali Radix, 6 g of Atractylodis Rhizoma alba, 6 g of Rehmanniae Rhizoma, 2 g of Zanthoxyli Fructus, 3 g of Magnoliae Flos, 5 g of Xanthii Fructus, 5 g of Mori Cortex Radicis, 4 g of Pinelliae Tuber, 3 g of Cimicifugae Rhizoma, 6 g of Puerariae Radix and 2 g of Menthae Herba. The obtained mixture was decocted and concentrated for 1.5 hour to obtain 150 ml of decoction.

EXAMPLE 2

Preparation of Decoction 1000 ml of water was added to the mixture including 5 g of Platycodi Radix, 3 g of Scutellariae Radix, 3 g of Ponciri Fructus, 3 g of Schizonepetae Herba, 3 g of Bupleuri Radix, 3 g of Angelicae dahuricae Radix, 5 g of Paeoniae Radix alba; 4 g of Cnidii Rhizoma, 6 g of Angelicae gigantis Radix, 2 g of Ledebouriellae Radix, 4 g of Forsythiae Fructus, 6 g of Glycyrrhizae Radix, 9 g of Lonicerae Flos, 10 g of Taraxaci Herba, 4 g of Trichosanthis Radix, 9 of Ulmi Cortex Radicis, 8 g of Astragali Radix, 6 g of Atractylodis Rhizoma alba, 6 g of Rehmanniae Rhizoma, 2 g of Zanthoxyli Fructus, 3 g of Magnoliae Flos, 5 g of Xanthii Fructus, 5 g of Mori Cortex Radicis, 4 g of Pinelliae Tuber, 3 g of Cimicifugae Rhizoma, 6 g of Puerariae Radix, 2 g of Menthae Herba, 4 g of Atractylodis Rhizoma, 4 g of Aurantii Nobilis Pericarpium, 4 g of Amomi Semen, 4 g of Myristicae Semen, 3 g of Mume Fructus, 2 g of Asiasari Radix, 3 g of Akebiae Caulis, 4 g of Raphani Semen and 8 g of Cocicis Semen. The obtained mixture was decocted and concentrated for 1.5 hour to obtain 15:0 ml of decoction.

EXAMPLE 3

Preparation of Other Formulation

The decoctions prepared by Examples 1 and 2 were formulated to pills, granules, spray, tablet, or capsules in accordance with conventional methods.

Test Example 1

Test for Toxic and Side Effects

The decoction prepared in Example, 2 were orally administrated to 30 white mature rats in a dose of 2 ml/kg, 10 ml/kg and 20 ml/kg which are 1, 2, 5 and 10 times, respectively, of human unit dose (that is, 1.5–2 ml per 1 kg of human body) for 90 days. Then, the subject rats were observed for 30 days every day. As a result, any apparent and physiological abnormality was not found in all experimental groups.

The present inventors have investigated the dose and administration route of the decoction for hundreds of patients (from 3 years old to adults) regardless of sex. As a result, the standard dose was determined, and the actual administrated doses were varied depending on age, etc. Local and systemic side effects were almost not found in patients, but a few patients experienced intestinal discomfort and temporal "Myunghyun" phenomenon (crisis for healing). Such intestinal discomfort above was disappeared after decreasing the dose to ½ to ⅔.

Test Example 2

Test of Clinical Effect on Allergic Diseases

This clinical test was carried out by administering the decoction according to Example 2 to about 500 patients suffering allergic diseases under the direction and inspection of the inventors at the pediatrics of Jeonju Herbal Medicine Hospital affiliated to Wonkwang University located in Jeonju-si, Jeonrabuk-do, Korea and at the otorhinolaryngology of Wonkwang Medical College Hospital located in Iksan-si, Jeonrabuk-do, Korea. Most of patients are 3 to 15 years old, and the duration of allergic diseases ranged 1 to 96 months. These patients are classified into temporary allergic patients (120) and chronic recurrent allergic patients (380). Most patients with allergic diseases such as allergic rhinitis, chronic recurrent paranasal sinusitis, recurrent otitis media with effusions, atopic dermatitis, chronic urticaria, and bronchial asthma were also suffering from edema, but a few patients were suffering the allergic diseases alone. Particular abnormalities were not found in general medical check-up. However, they are classified into the following groups: weak abdominal constitution group; weak pulmonary constitution group; and weak kidney constitution group by iris constitution diagnosis. They were also classified into a group having transformed somatide by in vivo blood analysis, a group that shows positive for antigen (35 kinds of respiratory allergens and 35 kinds of digestive allergens) and has increased value of IgE by MAST test in blood, a group showing hypertrophy of paranasal and inf. nasal concha mucous membranes by computed tomography (CT) or showing hypertrophy of inf. nasal concha by rhinoscopy, and a group that effusion was retained within the middle ear by otoscopy. The main cause of the allergic diseases was recognized to be the imbalance of immune system of organism. In particular, hypersensitive reactions to antigen and various virus were exhibited due to imbalance of Yang-Ki and Eum-Ki in digestive organs (spleen and stomach), respiratory organs (lungs), and urogenital organ (kidney). Anti-allergic drug such as antihistamine had no effect for most patients except temporal alleviation of symptoms since excessive antibiotics and steroid were administered to them for 1 to more than 3 years as a treatment of Western medicines.

The progresses of the diseases were watched at interval of 10 days after administrating 2 ml/kg of the decoction 3 times a day.

The medical effects of the present composition were evaluated by observation of improvement of symptoms several times every 10 days, by endoscopy once a week, by simple X-ray or CT once every 2 months; and by blood cell analysis once every 2 months. The results are as follows.

After the treatment duration of 96 days for 110 young children with chronic recurrent paranasal sinusitis (empyema), 90% of them were determined to be remission state on x-ray and CT, while 10% didn't show any improvements.

In 85% of 100 patients with allergic rhinitis, symptoms such as sneezing, rhinorrhea, nasal congestion, itching of nasal mucosa, and congestion and pruritis of conjunctiva were improved, and edema and secretion of nasal mucosa were decreased while, in about 10% of them, any effect was not found. For about 5% of them, a long period follow-up was not available.

As a result of diagnosis by simple X-ray and CT for about 80 young children (2 to 13 years old) with recurrent otitis media, 42% of them were accompanied with chronic paranasal sinusitis. As a result of diagnosis by simple X-ray and CT every 2 months, mucosal hypertrophy of paranasal sinus was decreased. It was shown that the effusion of middle ear was decreased or disappeared, and 83% of young patients with otitis media were cured after 1 to 3 months of treatment which was diagnosed by otoscopy. Simple X-ray or CT was taken every 2 months since cured otitis media could relapse due to cold when mucosal hypertrophy of paranasal sinus was not completely cured. It took 3 to 6 months for young children suffering from recurrent otitis media accompanied with chronic paranasal sinusitis to be cured for mucosal hypertrophy as well as otitis media.

Around 80% of patients with atopic dermatitis (ranging from 2 years old to adult) showed improved symptoms and curative effects after 3 to 6 month treatment, while 10% of them didn't show any improvement, and for the rest 10% of them, a long period of follow-up was not available.

For young children, bronchial asthma was accompanied with chronically recurrent paranasal sinusitis (so-called sinubronchitis) rather than the bronchial asthma was developed alone. For bronchial paranasal sinusitis, 82% of young patients ranging from 2 to 15 years old showed improved symptoms and curative effects after 2 to 6 month treatment, while 8% of them didn't show any changes. For the rest 10% of them, a long period of follow-up was not available.

Test Example 3

Simple X-ray and CT for the Curative Effect on Chronically Recurrent Paranasal Sinusitis (Empyema)

Simple X-ray has a drawback that false positive may be diagnosed and it is difficult to exactly tell acute disease from chronic disease. However, CT has not been used in the studies of herbal medical treatment for chronic paranasal sinusitis in Korea and foreign countries.

The present inventors used the simple X-ray together with CT to diagnose chronic paranasal sinusitis of young patients who visited the pediatrics of Jeonju Herbal Medicines Hospital affiliated with Wonkwang University and were suspected for chronic paranasal sinusitis in view of severe inflammation and a number of relapse. It was found that hypertrophied mucous membrane was recovered and clinical symptoms were resolved after the treatment by the decoction prepared in Example 2.

(1) Subjects

Simple X-rays were taken for 48 patients suffering from rhinitis who visited the pediatrics of Jeonju Herbal Medicines Hospital affiliated with Wonkwang University from February 1998 to March 1999. The patients consisted of 24 females and 24 males, and were 6.4 years old on the average (ranging from 3 to 13 years). While the morbid period ranging from 10 days to 48 months was 10.6 months on the average, and the treatment duration ranging from 25 days to 11 months was 3 months on the average. 30 young patients (63%) showed family histories within three degrees of kinship, and 31 ones (65%) showed respiratory allergies such as otitis media, allergic rhinitis, bronchiolitis and asthma, and digestive allergies such as milk allergy or hypersensitive colitis in the past.

CT scans were taken for 42 patients suffering from chronic paranasal sinusitis who visited the pediatrics of Jeonju Herbal Medicines Hospital affiliated with Wonkwang University for 9 months from December 1998 to August 1999. They were 21 female patients and 21 male ones, 6.7 years old on average (ranging from 4 to 13 years old) and the morbid period ranging from 10 days to 96 months was 4.2 months on the average, and treatment duration ranging from 28 to 200 days was 96 days on the average. 32 young patients (76%) had family histories related to the allergic disease, and 37 ones (88%) also showed respiratory allergies such as otitis media, allergic rhinitis, bronchiolitis and asthma, digestive allergies such as milk allergy or hypersensitive colitis, and dermal allergies such as atopic dermatitis and urticaria in the past.

(2) Changes Before and After the Treatment on Simple X-ray and CT

Simple X-rays were taken to inspect both sides of maxillary sinus, ethmoidal sinus, and frontal sinus from the Water's view. Young patients were divided into two groups, one group of patients suffering from respiratory allergies such as otitis, media, allergic rhinitis, bronchiolitis and asthma, and digestive allergies such as milk allergy or hypersensitive colitis in the past, and the other group without allergies. According to the degrees of X-ray shadow of paranasal sinus and bony hypertrophy, they are further classified into 4 levels (normal, mild, moderate, and severe). The criteria were as follows: Normal—shadow of paranasal sinus is the same as oral cavity or nasal cavity, or without a drastic distinction (0 points), Mild—hypertrophy of mucous membrane or bony hypertrophy is not seen conspicuously but its overall shadow increased (1 points), Moderate—hypertrophy of mucous membrane is distinct but limited to a part of paranasal sinus without bony hypertrophy (2 points), and Severe—hypertrophy of mucous membrane is seen overall when the shadow of air is not seen or bony hypertrophy is seen (3 points). Wilcoxon Signed Ranks Test was used to take statistics on points obtained discontinuously.

CTs were taken to inspect maxillary sinus and ethmoidal sinus in axial and coronal views at intervals of 2 cm to obtain three images. Frontal sinus and sphenoidal sinus were not inspected. However, some images of frontal sinus and sphenoidal sinus were taken in outside hospitals. CT scans for paranasal sinus were divided into 4 levels (normal, mild, moderate, and severe) based on thickness of mucous membrane and bony hypertrophy before and after the treatment. The criteria were as follows: Normal—thickness of mucous membrane of paranasal is below 3 mm and without hypertrophy (0 points), Mild—between 3 mm and 5 mm without bony hypertrophy (1 points), Moderate—between 5 mm and 1 cm without bony hypertrophy (2 points), and Severe—over 1 cm with bony hypertrophy (3 points). Wilcoxon Signed Ranks Test was used to take statistics on points. The treatment durations were determined according to presence or absence of allergy. The case that the severity level of paranasal sinusitis of two sides of maxillary sinus is different from each other was classified to a more severe level.

(3) Improvement of Symptoms

Symptoms were surveyed before and after the treatment. Simple X-ray group was surveyed backwardly (that is, the past symptoms of patients including their past history, family history and main symptom were surveyed), and CT group was surveyed forwardly (that is, the present symptoms of patients including their past history, family history and main symptom were surveyed).

(4) Effect of the Treatment for Empyema Diagnosed by Simple X-ray

Comparing simple X-ray images before the treatment with those after symptoms disappeared, 46 cases (96%) were cured, 2 cases (4%) didn't show any improvement, and any worsened case was not seen. When the frequency of inflammation was surveyed, the inflammation was found the most in maxillary sinus (100%), followed by ethmoidal sinus (50%) and maxillary sinus (17%). For the organs in which the inflammation remained after the treatment, ethmoidal sinus (12%) was the most, followed by maxillary sinus (4%) and frontal sinus (2%).

Treatment duration of the 46 patients was 89.3 days in diagnosis by simple X-ray images. For 28 patients who were in the severe level of mucous membrane for maxillary sinus, the duration was 93 days. For 15 patients who were in the moderate level of it, it was 68 days, and for 3 patients who were in the mild level, it was 75.5 days. It can be seen that the treatment duration of severe cases is longer than mild cases or moderate cases. For 23 patients who had inflammation in maxillary sinus and ethmoidal sinus, the treatment duration was 87.3 days, and for 25 patients who had inflammation only in maxillary sinus but none in ethmoidal sinus, the treatment duration was 76.5 days. Hence, it can be seen that the treatment duration of patients who had inflammation in ethmoidal sinus was longer. For 30 patients who had inflammation on both sides of maxillary sinus, the treatment duration was 84.3 days on the average. For 8 patients who had inflammation on the right maxillary sinus, the treatment duration was 61.6 days, and for 8 patients who had inflammation on the left maxillary sinus, the treatment duration was 63.6 days. Hence, it can be seen that patients who had inflammation on both sides of maxillary sinus had longer treatment duration.

Before the treatment, the degree of hypertrophy of mucous membrane in maxillary sinus was that 30 patients were serious, 15 moderate, 3 mild, and none normal. However, after the treatment, 2 cases were serious, 2 moderate, 26 mild, and 18 normal.

(5) Effect of the Treatment for Empyema Diagnosed by CT

Comparing simple X-ray images before the treatment with those after the treatment, 38 cases (90%) were cured and 2 cases (5%) didn't show any change. The case that the thickness of mucous membrane became thinner from CT image but didn't change to severe, moderate, or mild level, were classified into no change group. It took 93.7 days for the 38 patients to be cured on the average. Among cured 35 cases, for 29 patients whose mucous membrane hypertrophy was a severe level, the treatment duration was 104.9 days, and for 9 patients whose mucous membrane hypertrophy was moderate level, the treatment duration was 73 days. For 30 patients who had inflammation in both ethmoidal sinus and maxillary sinus, the treatment duration was 99 days, but for 12 patients who didn't have inflammation in ethmoidal sinus, treatment duration was 49 days. Hence, it can be seen that the treatment duration for patients who had inflammation in ethmoidal sinus was 50 days longer. For 28 patients who had inflammation on both sides of maxillary sinus, the treatment duration was 98.5 days, for 6 patients who had inflammation on the right maxillary sinus, the treatment duration was 76.7 days, and for 4 patients who had inflammation on the left maxillary sinus, the treatment duration was 58 days. Hence, it can be seen that the treatment duration of patients who had inflammation on both sides was 30 days longer than the others.

In 2 cases (5%), hypertrophy of mucous membrane became more serious after the treatment on CT scan. Before the treatment, the degrees of hypertrophy of mucous membrane in maxillary sinus were as follows: 30 patients were serious, 10 moderate, 2 mild, and none normal. After the treatment, 6 patients were serious, 6 mild, and 30 normal. When 0 point is given to normal cases, 1 point to mild ones, 2 point to moderate ones, and 3 point to serious ones, and then statistics was taken, a statistic significance was shown ($P<0.005$).

(6) Effect of the Treatment According to Whether or not Allergy is Accompanied

In case of simple X-ray, the average treatment duration of the 31 patients who had allergy was 84.6 days, and that of the 17 patients who had no allergy in the past was 98.5 days. Those who did not have allergy had longer treatment duration, and 2 patients who were not cured had allergy in the past.

On the other hand, in case of CT, it took 110.8 days for 37 patients who had allergy to be cured on the average, and it took 40.6 days for 5 patients who didn't have allergy in the past. Those who did not have allergy had a shorter period of treatment, and 4 patients who were not cured all have allergies. (7) Symptom Improvement Rate The symptoms of 48 subjects in simple X-ray group were coughing in the morning and evening (63%), nasal obstruction (63%), rhinorrhea (54%), swollen throat stimulated by continuous postnasal discharge (52%), symptom that nasal mucus goes down the throat (48%), nasal bleeding (24%), headache (17%), mouth breathing (12%), and snoring (6%). The symptoms of 42 patients in CT group were nasal obstruction (83%), rhinorrhea (71%), coughing in the morning and evening (69%), tonsillar hypertrophy due to persistent postnasal discharge (57%), postnasal discharge (50%), snoring (38%), headache (31%), and nasal bleeding (19%).

The whole symptoms in 90 patients were nasal obstruction (72%) that was the most frequent, coughing (69%), rhinorrhea (62%), pharyngeal tumor due to chronic lymph follicle irritation by postnasal discharge (54%), postnasal discharge (49%), mouth breathing (28%), and headache (23%).

60% of the patients showed a symptomatic improvement after 1–2 month treatment and 90% also showed improvement after 2–4 month treatment. However, 10% of patients didn't show any improvement after the treatment.

(8) Frequency of Prescription

If paranasal sinusitis was diagnosed in simple X-ray group, the present composition was prescribed (81%). If paranasal sinusitis was diagnosed in CT scan group, the present composition was also prescribed (77%). The present composition was also used for 90 patients with rhinitis (81%).

(9) Results

By internal treating with the present composition prepared in Example 2, 95% of patients showed symptomatic improvement, which was proved by X-ray and CT-scan. It seems that herb medication is an essential treatment for minimizing the recurrence of chronic paranasal sinusitis by enhancing the immunity, improving the mucosal a hypertrophy and allergy, and increasing the defense mechanism for URI. It is reported that chronic paranasal sinusitis has a higher recurrence rate despite proper medical treatment or even operation. Among 90 patients with chronic paranasal sinusitis clinically, 38 patients whose CT scan showed chronic mucosal hypertrophy and 46 patients whose simple X-ray showed chronic change without air fluid level (sign of acute sinusitis) made improvement. Therefore, it is concluded that the present composition has good effects in treating chronic paranasal sinusitis by enhancing general immunity, suppressing allergy, and restoring hypertrophied mucosa.

Test Example 4

Analysis of Cell-activating Substance in the Middle-ear Fluid

Recently, importance of immune mechanism as a cause of otitis media has been getting more attentions. Cell-activating substances, cytokines, are involved in host defense mechanism against infection or inflammation and also in tissue destruction as inflammation and immune response-mediating materials. Among these substances, interleukin. (IL)-1 has been measured to be high in the early-stage of otitis media, IL-6 producing specific antibody in immune cells play a role in removing bacteria and bacteria-secreting materials in the middle ear, and TNF-$\alpha$ has been measured to be higher as the duration of disease is longer. Thus, it was found that cell-activating substances are involved in pathogenesis of several disease and drugs controlling these substances have potency for therapeutic agent.

The present inventors have studied the effects of the present composition on cell-activating substance within the middle ear by comparing the amount of IL-1, IL-2, IL-6 and TNF-$\alpha$ in the middle-ear fluid from the patient having otitis media administrated with the present composition and from the patient having otitis media administrated with antibiotics. In conclusion, significant results were obtained.

(1) Subjects 17 patients with ROME who visited the otorhinolaryngology department of ENT in the hospital of Wonkwang medical school from September 1997 to May 1999, were divided into two groups; Antibiotics group including 10 patients (13 ears) who were administrated antibiotics therapy (each of Augmentin syrup, Cefzil syrup, and Lorabid syrup was administrated for a week) for 2–6 months and the herbal medicine group including 7 patients (11 ears) who were administrated with the present composition for 17 months at the oriental hospital of Wonkwang university. The middle ear fluid of the patients that were taken by tympanic membrane puncture or ventilation tube insertion was analyzed. Samples were divided into serous effusion (11 ears) and mucous effusion (13 ears) by apparent morphology. Age distribution is as follows: 3 ears from birth to 5 year, 18 ears from 6 year to 10 year, and 3 ears above 11 year. The morbid period was defined as from onset to operation. 2 groups were divided according to preoperative treatment: the herbal medicine group (11 ears) and antibiotics group (13 ears). Also, some patients (8 ears) had a past history of tympanotomy or tube insertion, and other patients (16 ears) had no past history.

(2) Collecting the Middle-ear Fluid

The middle-ear fluids were collected aseptically from the antibiotic group (13 ears) and the herbal medicine group (11 ears) after tympanotomy. After adding PBS buffering solution to the middle ear fluids, the middle ear fluids were centrifuged at 2000 rpm for 10 minutes. Then, the obtained supernatants were lyophilized and melted by the same volume of PBS buffer-solution and stored. at −70° C. The quantification was done after these steps.

(3) Quantification of Cell-activating Substances

ELISA (Enzyme-linked immunosorbent assay) method was used for quantification of cell-activating substances and carried out in duplicate in 96 well ELISA plate. 100 µl of monoclonal antibodies (1 µg/ml) for each cell-activating substance diluted with PBS (pH 7.4) were coated in 96 well plate and stored at 4° C. for 12 hours. After washing this plate with PBS containing 0.05% Tween, a blocking process was done with PBS solution containing 1% BSA, 5% sucrose, and 0.05% $NaN_3$ for 1 hour. After washing the plate several times, samples that were prepared by melting the lyophilized exudates with PBS that were collected from the ears of patients with otitis media, and standard cell-activating substance were added to the plate and the plate was stored at 37° C. for 2 hours. Then, after washing each well, 0.2 µg/ml of biotin-binded antibody was added to the plate and the plate was stored at 37° C. for 2 hours again. After washing the plate, avidine peroxidase was added to each well, and the plate was stored at 37° C. for 20 minutes. After washing the wells, and ABTS substrate was added and color reaction was measured at 405 mm by ELISA reader. The BCA methods were used for measuring the total protein in middle ear fluids.

(4) Analysis

Buffer solution was added to all of the middle-ear fluids because they had such high viscosity that the concentration and dose were not easily measured. Then, through measuring cell-activating substance and total protein level, the analyzed unit would be cell-activating substance. (pg)/total protein (mg). The amount of IL-2, IL-4, IL-6, and TNF-α in the herbal medicine group and the antibiotic group were analyzed, and also the amounts of IL-2, IL-4, IL-6, and TNF-α in the serous effusion group and the mucous effusion group.

(5) Results

Effusion was collected from ears of a group of patients suffering from ROME administered with antibiotics (the antibiotic group) and the other group of patients suffering from ROME administered with the present composition (the herbal medicine group), and cell-activating substances that were related to specific and non-specific immune reaction were quantified through the ELISA method.

a. The amounts of cell-activating substances in the herbal medicine group and the antibiotic group were compared in Table 1.

TABLE 1

|  | IL-2 | IL-4 | IL-6 | TNE-α |
|---|---|---|---|---|
| Herbal Medicine Group (pg/ml) | 1024.11 | 159 | 1246 | 61.09 |
| Antibiotic Group (pg/ml) | 207.25 | 82.91 | 2651.8 | 219.9 |

That is, IL-2 and IL-4 had higher values in the herbal medicine group, while IL-6 and TNF-α were higher in the antibiotic group.

b. Table 2 shows values of IL-2 divided by TP.

TABLE 2

|  | Highest values | Lowest values | Average |
|---|---|---|---|
| Herbal Medicine Group (pg/mg) | 19.44 | 0.236 | 5.85 ± 2.35 |
| Antibiotic Group (pg/mg) | 2.36 | 0.063 | 0.761 ± 0.25 |

The Herbal medicine group showed significantly higher values than the antibiotic group ($P<0.05$).

c. Table 3 shows values of IL-4 divided by TP.

TABLE 3

|  | Highest value | Lowest value | Average |
|---|---|---|---|
| Herbal Medicine Group (pg/mg) | 2.642 | 0.299 | 1.10 ± 0.255 |
| Antibiotic Group (pg/mg) | 0.656 | 0.196 | 0.39 ± 0.038 |

The herbal medicine group showed significantly higher values than the antibiotic group ($P<0.01$).

d. Table 4 shows values of IL-6 divided by TP.

TABLE 4

|  | Highest value | Lowest value | Average |
|---|---|---|---|
| Herbal Medicine Group (pg/mg) | 21.719 | 0.674 | 7.329 ± 2.73 |
| Antibiotic Group (pg/mg) | 30.273 | 0.154 | 10.23 ± 3.12 |

The herbal medicine group showed significantly lower values than the antibiotic group ($P<0.05$).

e. Table 5 shows values of TNF-α divided by TP.

TABLE 5

|  | Highest value | Lowest value | Average |
|---|---|---|---|
| Herbal Medicine Group (pg/mg) | 1.707 | 0.011 | 0.39 ± 0.19 |
| Antibiotic Group (pg/mg) | 1.622 | 0.479 | 1.07 ± 0.1375 |

The herbal medicine group showed significantly lower values than the antibiotic group ($P<0.01$).

f. Effusions of the herbal medicine group and the antibiotic group were classified into the serous effusion group and the mucous effusion group, and cell-activation substances and their protein values were compared with each other.

| | | Herbal Medicine Group (11 ear) | | Antibiotic Group (13 ear) | |
|---|---|---|---|---|---|
| Unit: pg/mg | | The serous effusion group (3 ear) | The mucous effusion group | The serous effusion group (8 ear) | The mucous effusion |
| IL-2/TP | Highest value | 7.91 | 19.44 | 2.36 | 1.81 |
| | Lowest value | 0.54 | 0.23 | 0.068 | 0.063 |
| | Average | 3.611 | 6.966 | 0.62 | 1.008 |
| IL-4/TP | Highest value | 2.52 | 2.64 | 0.45 | 0.65 |
| | Lowest value | 0.76 | 0.299 | 0.19 | 0.237 |
| | Average | 1.686 | 0.888 | 0.337 | 0.46 |
| IL-6/TP | Highest value | 9.56 | 21.70 | 30.27 | 19.57 |
| | Lowest value | 1.25 | 0.674 | 0.15 | 0.521 |
| | Average | 4.335 | 8.703 | 11.45 | 8.5 |
| TNF-α/ | Highest value | 1.70 | 0.937 | 1.91 | 1.62 |

-continued

|  | Unit: pg/mg | Herbal Medicine Group (11 ear) | | Antibiotic Group (13 ear) | |
| --- | --- | --- | --- | --- | --- |
|  |  | The serous effusion group (3 ear) | The mucous effusion group | The serous effusion group (8 ear) | The mucous effusion |
| TP | Lowest value | 0.013 | 0.011 | 0.62 | 0.479 |
|  | Average | 1.048 | 0.144 | 1.13 | 0.99 | g. Clinical surveys were done with respect to exudate morphology in infant with ROME, morbid period, accompanying of chronic paranasal sinusitis, and existence of preoperative mpanotomy or ventilation tube insertion. The results were as follows.

Regarding exudates morphology, serous effusion was higher in antibiotic group (61.5%) and, mucous effusion was higher in the herbal medicine group (72.7%). Regarding morbid period, patients within 3 months were higher in the antibiotic group (53.8%) while patients more than 3 months was higher in the herbal medicine group (81.8%). In regard to accompanying chronic paranasal sinusitis, the percentage of patients accompanied by chronic paranasal sinusitis was 76.9% in the antibiotic group, and 81.8% in the herbal medicine group. Regarding existence of preoperative tympanotomy or ventilation tube insertion, patients with history of preoperative tympanotomy or ventilation tube insertion were 7.69% in the antibiotic group and 63.6% in the herbal medicine group.

(6) Results

As a result, it was found that IL-2 and IL-4 of the herbal medicine group administered with the present composition were increased remarkably compared with the antibiotic group while IL-2 and IL-4 participating in specific immune response was decreased drastically when patients were still suffering from otitis media even after administered with antibiotic and treated with conservative therapy which was shown in the study of Okamoto et al. In particular, IL-2 serves for antibody to be properly produced with controlling the function of B cells as it is the first indication of cell activation and producing IL-2 receptor and promoting its own secretion with the function of autocrine, while it is expected that, as IL-4 induces the anti-tumor activity through drastic infiltration of cytotoxic eosinophil into the region of tumor, the increase of these cell-activating substances will make an important part in improving otitis media.

It can be seen that cell-activating substances, TNF-α and IL-6, which have a direct relation to inflammatory reaction were increased in patients with otitis media contrary to IL-2 and IL-4. These cell-activating substances showed a drastic decrease in the herbal medicine group administered with the composition of this invention, compared with the antibiotic group. The concentration of IL-6 was measured higher in the mucous effusion group than the serous effusion group. It is assumed by some reports that the concentration of IL-6 is related to improvement of recurrent otitis media. The mechanism that recurrent otitis media is cured in herbal medicine group of this study is considered to be a meaningful decrease of IL-6. It has been known that TNF-α is related to chronicity as it was measured highly in chronic ROME group with a long period of contraction and in relapse group subjected to ventilation tube insertion more than 2 times.

From the description above, it may be inferred that the composition of this invention has more excellent treatment effect on recurrent otitis media than the antibiotic group.

From clinical surveys for young child patients, serous effusion was higher in the antibiotic group (61.5%), while mucous effusion was higher in the herbal medicine group (72.7%). Regarding morbid period, patients within 3 months were higher in the antibiotic group (53.8%) while period more than 3 months was higher in herbal medicine group (81.8%). Regarding existence of preoperative tympanotomy or ventilation tube insertion, patients with history of preoperative tympanotomy or ventilation tube insertion was 7.69% in the antibiotic group and 63.6% in the herbal medicine group. Regarding whether or not chronic paranasal sinusitis was accompanied, the percentage of patients accompanied by chronic paranasal sinusitis was 76.9% in the antibiotic group, and 63.6% in the herbal medicine group. In spite of the fact, the percentage of cell-activating substances in the herbal medicine group was higher than in the antibiotic group. Hence, it can be seen that the composition of this invention has an excellent treatment effect on recurrent otitis media of young children.

Besides, 79.1% of young patients with recurrent otitis media were accompanied with chronic paranasal sinusitis, which shows that chronic paranasal sinusitis has a close relation to recurrent otitis media.

From these overall results, it is found that the pharmaceutical composition of this invention serves as an effective prescription for cure of patients with otitis media by controlling production of cell-activating substances participating in inflammatory reaction. More studies should be done on reaction mechanism through which the present prescription controls production of cell-activating substances in otitis media.

Effects of the Invention

As can see from the above experiments, the pharmaceutical composition of this invention can be effectively used as the preventative and curative substances for allergic diseases such as acute and chronic allergic rhinitis (including chronic paranasal sinusitis), allergic dermatitis, allergic otitis media (including recurrent otitis media), allergic conjunctivitis, and allergic asthma.

What is claimed is:

1. A pharmaceutical composition for preventing and treating allergic diseases comprising the extract of mixture including Platycodi Radix, Scutellariae Radix, Ponciri Fructus, Schizonepetae Herba, Bupleuri Radix, Angelicae dahuricae Radix, Paeoniae Radix alba, Cnidii Rhizoma, Angelicae gigantis Radix, Ledebouriellae Radix, Forsythiae Fructus, Glycyrrhizae Radix, Lonicerae Flos, Taraxaci Herba, Trichosanthis Radix, Ulmi Cortex Radicis, Astragali Radix, Atractylodis Rhizoma alba, Rehmanniae Rhizoma, Zanthoxyli Fructus, Magnoliae Flos, Xanthii Fructus, Mori Cortex Radicis, Pinelliae Tuber, Cimicifugae Rhizoma, Puerariae Radix and Menthae Herba.

2. The pharmaceutical composition according to claim 1 wherein the allergic diseases are chronic or acute allergic rhinitis, chronic paranasal sinusitis, allergic dermatitis, allergic otitis media, allergic conjunctivitis or allergic asthma.

3. The pharmaceutical composition according to claim 1 wherein the mixture further comprises more than one selected from a group consisting of Atractylodis Rhizoma, Aurantii Nobilis Pericarpium, Amomi Semen, Myristicae Semen, Mume Fructus, Asiasari Radix, Akebiae Caulis, Raphani Semen and Coicis Semen.

4. The pharmaceutical composition according to claim 1 wherein the mixture contains Platycodi Radix, Scutellariae Radix, Ponciri Fructus, Schizonepetae Herba, Bupleuri Radix, Angelicae dahuricae Radix, Paeoniae Radix alba, Cnidii Rhizoma, Angelicae gigantis Radix, Ledebouriellae Radix, Forsythiae Fructus, Glycyrrhizae Radix, Lonicerae Flos, Taraxaci Herba, Trichosanthis Radix, Ulmi Cortex Radicis, Astragali Radix, Atractylodis Rhizoma alba, Rehmanniae Rhizoma, Zanthoxyli Fructus, Magnoliae Flos, Xanthii Fructus, Mori Cortex Radicis, Pinelliae Tuber, Cimicifugae Rhizoma, Puerariae Radix and Menthae Herba in a ratio of 4–6:2–4:3:3:3:3:4–6:4:4–8:2:2–6:4–8:6–12:8–12:4:6–12:6–10:4–8:4–8:2:2–4:4–6:4–6:4:2–4:4–8:2.

5. A pharmaceutical composition for preventing and treating allergic diseases comprising a mixture containing Atractylodis Rhizoma, Aurantii Nobilis Pericarpium, Amomi Semen, Myristicae Semen, Mume Fructus, Asiasari Radix, Akebiae Caulis, Raphani Semen and Coicis Semen in a ratio of 4:4:4:4:2–4:2:3:4:8–10.

6. A method for preparing the pharmaceutical composition according to claim 1 comprising the step of mixing the extract of mixture including Platycodi Radix, Scutellariae Radix, Ponciri Fructus, Schizonepetae Herba, Bupleuri Radix, Angelicae dahuricae Radix, Paeoniae Radix alba, Cnidii Rhizoma, Angelicae gigantis Radix, Ledebouriellae Radix, Forsythiae Fructus, Glycyrrhizae Radix, Lonicerae Flos, Taraxaci Herba, Trichosanthis Radix, Ulmi Cortex Radicis, Astragali Radix, Atractylodis Rhizoma alba, Rehmanniae Rhizoma, Zanthoxyli Fructus, Magnoliae Flos, Xanthii Fructus, Mori Cortex Radicis, Pinelliae Tuber, Cimicifugae Rhizoma, Puerariae Radix and Menthae Herba, with pharmaceutically acceptable carriers.

7. A method for preparing a pharmaceutical composition comprising a step of mixing an extract of mixture including Platycodi Radix, Scutellariae Radix, Ponciri Fructus, Schizonepetae Herba, Bupleuri Radix, Angelicae dahuricae Radix, Paeoniae Radix alba, Cnidii Rhizoma, Angelicae gigantis Radix, Ledebouriellae Radix, Forsythiae Fructus, Glycyrrhizae Radix, Lonicerae Flos, Taraxaci Herba, Trichosanthis Radix, Ulmi Cortex Radicis, Astragali Radix, Atractylodis Rhizoma alba, Rehmanniae Rhizoma, Zanthoxyli Fructus, Magnoliae Flos, Xanthii Fructus, Mori Cortex Radicis, Pinelliae Tuber, Cimicifugae Rhizoma, Puerariae Radix and Menthae Herba along with more than one selected from a group consisting of Atractylodis Rhizoma, Aurantii Nobilis Pericarpium, Amomi Semen, Myristicae Semen, Mume Fructus, Asiasari Radix, Akebiae Caulis, Raphani Semen and Coicis Semen with pharmaceutically acceptable carriers.

* * * * *